(12) United States Patent
Strobel et al.

(10) Patent No.: US 7,326,689 B2
(45) Date of Patent: Feb. 5, 2008

(54) PSEUDOMYCINS USEFUL AGAINST PLANT DISEASES

(75) Inventors: Gary Strobel, Bozeman, MT (US); Michael J. Rodriguez, Indianapolis, IN (US)

(73) Assignees: Eli Lilly and Company, Indianapolis, IN (US); Montana State University, Bozeman, MT (US)

( * ) Notice: Subject to any disclaimer, the term of this patent is extended or adjusted under 35 U.S.C. 154(b) by 585 days.

(21) Appl. No.: 10/343,199

(22) PCT Filed: Aug. 17, 2001

(86) PCT No.: PCT/US01/25724

§ 371 (c)(1),
(2), (4) Date: Aug. 18, 2003

(87) PCT Pub. No.: WO02/15696

PCT Pub. Date: Feb. 28, 2002

(65) Prior Publication Data

US 2004/0029797 A1    Feb. 12, 2004

Related U.S. Application Data

(60) Provisional application No. 60/226,010, filed on Aug. 18, 2000.

(51) Int. Cl.
| | |
|---|---|
| *C12N 1/20* | (2006.01) |
| *C12P 1/04* | (2006.01) |
| *C12P 7/00* | (2006.01) |
| *C12P 7/02* | (2006.01) |
| *C12P 15/00* | (2006.01) |
| *C12P 21/04* | (2006.01) |
| *A61K 38/00* | (2006.01) |

(52) U.S. Cl. ........................ 514/15; 435/71.3; 435/170; 435/253.3; 435/822; 435/874; 514/11; 530/328

(58) Field of Classification Search ...................... None
See application file for complete search history.

(56) References Cited

U.S. PATENT DOCUMENTS

| | | | | |
|---|---|---|---|---|
| 4,342,746 | A | 8/1982 | Strobel | 424/93 |
| 4,798,723 | A | 1/1989 | Dart et al. | 424/93 |
| 5,576,298 | A | 11/1996 | Strobel et al. | 514/15 |
| 5,602,097 | A | 2/1997 | Edwards | 514/17 |
| 5,837,685 | A | 11/1998 | Strobel et al. | 514/15 |
| 5,885,782 | A | 3/1999 | Edwards | 435/7.1 |
| 6,017,752 | A | 1/2000 | Janisiewicz et al. | 435/267 |
| 6,630,147 | B1 * | 10/2003 | Kulanthaivel et al. | 424/184.1 |

FOREIGN PATENT DOCUMENTS

| | | |
|---|---|---|
| EP | 0 683 980 A | 11/1995 |
| GB | 2 288 980 A | 11/1995 |
| WO | WO 98 57174 A | 12/1998 |
| WO | WO 00 63237 A | 10/2000 |
| WO | WO 00 63345 A | 10/2000 |

\* cited by examiner

*Primary Examiner*—David M. Naff
*Assistant Examiner*—Deborah K. Ware
(74) *Attorney, Agent, or Firm*—Woodard, Emhardt, Moriarty, McNett & Henry LLP

(57) ABSTRACT

Plants and crops subject to attack by fungal related diseases are protected or treated by the application of *Pseudomycin* compositions which were originally isolated from *Pseudomonas syringae*.

11 Claims, No Drawings

SEQUENCE LISTING

```
<160> NUMBER OF SEQ ID NOS: 1

<210> SEQ ID NO 1
<211> LENGTH: 9
<212> TYPE: PRT
<213> ORGANISM: Artificial Sequence
<220> FEATURE:
<223> OTHER INFORMATION: Synthesized Construct
<220> FEATURE:
<221> NAME/KEY: VARIANT
<222> LOCATION: 2
<223> OTHER INFORMATION: Xaa = Dbu
<220> FEATURE:
<221> NAME/KEY: VARIANT
<222> LOCATION: 5
<223> OTHER INFORMATION: Xaa = Dbu
<220> FEATURE:
<221> NAME/KEY: VARIANT
<222> LOCATION: 6
<223> OTHER INFORMATION: Xaa = alloThreonine
<220> FEATURE:
<221> NAME/KEY: VARIANT
<222> LOCATION: 7
<223> OTHER INFORMATION: Xaa = Dehydro-Abu
<220> FEATURE:
```

```
<221> NAME/KEY: VARIANT
<222> LOCATION: 8
<223> OTHER INFORMATION: Xaa = 3-hydroxyAspartic Acid
<220> FEATURE:
<221> NAME/KEY: VARIANT
<222> LOCATION: 9
<223> OTHER INFORMATION: Xaa = 4-chloroThreonine

<400> SEQUENCE: 1

Ser Xaa Asp Lys Xaa Xaa Xaa Xaa Xaa
1               5
```

PSEUDOMYCINS USEFUL AGAINST PLANT DISEASES

CROSS-REFERENCE TO RELATED APPLICATIONS

This application claims priority to PCT Application US01/25724, filed Aug. 17, 2001, and to U.S. Provisional Application Ser. No. 60/226,010, filed Aug. 18, 2000.

FIELD OF THE INVENTION

The present invention relates to the use of pseudomycins as effective fungicides against plant and crop diseases, and more particularly relates to the use of pseudomycins against particular classes of fungi which cause diseases in plants and crops.

BACKGROUND

One class of new antifungal agents, the pseudomycins, shows great promise for treating fungal infections in a variety of patients. (see i.e., Harrison, L., et al., "Pseudomycins, a family of novel peptides from *Pseudomonas syringae* possessing broad-spectrum antifungal activity," *J. Gen. Microbiology* 137(12), 2857-65 (1991) and U.S. Pat. Nos. 5,576,298 and 5,837,685). Pseudomycins are natural products derived from isolates of *Pseudomonas syringae*. *P. syringae* is a large group of plant-associated bacteria that have been the source of several bioactive substances, such as bacitracin and the syringomycins. Natural strains and transposon-generated mutants of *P. syringae* produce compounds with antifungal activity. A transposon-generated regulatory mutant of the wild type strain of *P. syringae* MSU 174, known as MSU 16H (ATCC 67028), produces several pseudomycins. Pseudomycins A, B, C and C' have been isolated, chemically characterized, and shown to possess wide spectrum antifungal activity, including activity against important fungal pathogens in both humans and plants. The pseudomycins are structurally related to but are distinct from syringomycin and other antimycotics from isolates of *P. syringae*. The peptide moiety for pseudomycins A, B, C, C' corresponds to L-Ser-D-Dab-L-Asp-L-Lys-L-Dab-L-aThr-Z-Dhb-L-Asp(3-OH)-L-Thr(4-Cl) with the terminal carboxyl group closing a macrocyclic ring on the OH group of the N-terminal Ser. The analogs are distinguished by the N-acyl side chain, i.e., pseudomycin A is N-acylated by 3,4-dihydroxytetradeconoate, pseudomycin B by 3-hydroxytetradecanoate, pseudomycin C by 3,4-dihydroxyhexadecanoate and pseudomycin C' by 3-hydroxyhexadecanoate. (see i.e., Ballio, A., et al., "Novel bioactive lipodepsipeptides from *Pseudomonas syringae*: the pseudomycins," *FEBS Letters*, 355(1), 96-100, (1994) and Coiro, V. M., et al., "Solution conformation of the *Pseudomonas syringae* MSU 16H phytotoxic lipodepsipeptide Pseudomycin A determined by computer simulations using distance geometry and molecular dynamics from NMR data," *Eur. J. Biochem.*, 257(2), 449-456 (1998).)

The present invention provides a group of pseudomycins which are particularly useful to protect plants and crops against fungal diseases.

SUMMARY OF THE INVENTION

It is an object of the present invention to provide a method for the treatment or protection of plants and crops against diseases.

A further object of the invention is to provide a method for the treatment or protection of plants and crops by application of certain pseudomycins.

An even further object of the invention is the use of certain pseudomycins to protect or treat plants and crops against diseases caused by fungi.

Other objects and advantages of the invention will become apparent as the description of the invention proceeds.

In satisfaction of the foregoing objects and advantages, the present invention provides a method for the protection or treatment of plant and crops against fungal-related diseases, which comprises applying to said plants or crops an effective amount of one or more pseudomycin products.

DESCRIPTION OF THE PREFERRED EMBODIMENTS

The present disclosure relates to the discovery of novel, previously unsuspected uses for the class of lipopeptides known collectively as the pseudomycins as fungicides or antimycotic agents. In a preferred embodiment, the pseudomycins, are individually and as a group, particularly useful in the treatment or protection of plants challenged by a group of Ascomyceteous fungi related to *Mycosphaerella* asp. (perfect or sexual stage of the fungus) and virtually all of the various imperfect stages of this fungus that are known, including *Septoria* sp., and *Cercospora* sp. In addition, a number of other extremely economically important plant pathogenic fungi are killed by the pseudomycins including *Tapesia yallundae*, *Ustilago maydis*, *Penicillum roqueforti*, *Monilinia* sp. and *Geotrichum candidum*. Thus, the pseudomycins, alone or individually, have use in treating plants to protect them from harm caused by these fungi.

The types of diseases caused by these organisms range from plants in storage (fruits and vegetables) to extremely important field diseases such as Black Sigatoka of banana and straw breaker and blotch of wheat.

This discovery relates to a previously unsuspected set of extremely important plant pathogenic fungi that seem to be biologically related and are sensitive to one or more of the pseudomycins and are both inhibited and killed by them. These fungi and a few others, not previously disclosed, cause some of the most important plant diseases on the planet. Currently these fungal-caused diseases are being controlled by simple or more complex mixtures of man-made fungicides which cause environmental damage and may be an unsuspected threat to human health. The pseudomycins, on the other hand, offer a safe, and effective alternative to the use of man-made chemicals for the control of certain plant diseases. In addition, the use of the pseudomycins for plant disease control have certain benefits since the use of natural products for disease control would allow the producer to proclaim that the crop has been grown under biological/organic conditions allowing for a higher profit to be made on the product. This is noteworthy since no major crop in the world currently has applied to it any naturally produced fungicide for plant disease control. The pseudomycins certainly offer many benefits to both the agricultural producer as well as the consumer.

As an example of how and why the pseudomycins may be useful to the world's agriculture, the minimum inhibitory concentrations(MICs) for several of the pseudomycins e.g. Pseudo A, B, B'C, and C' are in the range of 1 mg or less per ml. This is an extremely desirable concentration for effective application in agricultural situations. These compounds produce an even greater effect (less than 1.0 mg) when tested against *M. fijiensis* isolate 8088/88. *M. fijiensis* is the causal organism of the Black Sigatoka disease of bananas and plantains. Currently, the producers of these crops, worldwide, must spray a mixture of three fungicides (man-made) at the rate of 30 times per year in order to have a banana crop. This one disease alone represents the largest consumption of fungicide per crop in the entire world. The disadvantages for the use of these synthetic fungicides are numerous including: 1. their extremely high cost ($ millions); 2. the inability of the producer to sell organically grown produce since fungicides have been applied to it; and 3. the uncertainty to human as well the environmental health risks involved in the continuous use of the fungicides over decades. The soil beneath the banana canopy in the plantations appears sterile of animal life and shows a build up of fungicide residues. On the other hand, the naturally produced pseudomycins appear more effective in controlling the sigatoka disease, while at the same time offering benefits to the environment and to human health.

In addition, the pseudomycins are effective against a number of other plant disease causing fungi including the fingi that destroy plant produce in storage e.g. *Penicillium* sp., *Monilinia* sp. and *Geotrichum* sp. A mixture of pseudomycins applied to harvested fruit would preclude fungal infections and storage rots.

Still other possibilities for the applications of the pseudomycins include applications for the control of diseases caused by *Septoria* sp., specifically *S. nodurum* and *S. triticii* on wheat, but also, based on the biological activity of these molecules-virtually any *Septoria* sp. causing any plant disease in the world. Likewise, other fungi related to *Mycosphaeella* sp. are affected and they include plant diseases caused by *Cercospora* sp. which causes leaf spot of sugar beets and many other crops. Other disease causing organisms are also affected by the pseudomycins and they include *Dreschslera portulaceae*.

In accordance with the present invention it has been discovered that the pseudomycins described herein possess enormous antimycotic activity against a previously unsuspected, and closely related group of plant pathogenic fungi. This main group is represented by the perfect stage fungus sp. *Mycosphaeella* sp. and each of its representatives in the imperfect stage(asexual stage) such as *Septoria* sp. and *Cercospora* sp. Generally, the pseudomycins may be used alone or as a mixture in a formulation to protect plants from fungal infection. Applications to crops in the field as well as in storage are visualized as the potential uses of these compounds.

Thus, it is a purpose of this invention to demonstrate that a number of extremely economically important plant pathogenic fungi are susceptible to the effects of one or more pseudomycins which were originally isolated from the plant associated bacterium-*Pseudomonas syringae*.

The pseudomycins useful in the method of the present invention are preferably pseudomycins produced by the *Pseudomonas syringae* including the pseudomycins identified as *Pseudomycins* A, A' B, B' C and C' as well as derivatives such as pseudomycin A-PO4, a phosphate derivative and pseudomycin A-FB, both of which are known.

These pseudomycins are applied against a wide variety of plants and crops which are susceptible to parasitic diseases caused by fungi. In that connection, the pseudomycin compositions of the present invention are primarily useful to prevent the onset of parasitic diseases caused by fungi so that treatment of the plants and crops prior to onset of the disease is preferred. However, the pseudomycin compositions are also useful in treatment of infected plants.

Pseudomycin compositions of the present invention are effective at very low concentrations on the order of 1 up to 100 micrograms of pseudomycin per ml of aqueous solution. In that regard, a preferred method of application of the pseudomycin composition of this invention is by treatment as by spraying directly onto the plant or crop to be treated using the indicated concentrations. The pseudomycin compositions of the present invention may be in the form of solutions, suspensions or emulsions, or any other form suitable for spraying onto the plants and crops.

The preferred pseudomycins used in the present invention and their methods of preparation are known or are fully disclosed and described in copending applications PCT/US00/08728, filed Apr. 14, 2000 and PCT/US00/08727, filed Apr. 14, 2000 both applications designating the United States. The disclosures of both these applications are incorporated herein by reference in their entirety.

As used herein, the term "pseudomycin" refers to compounds having the following formula I:

where R is a lipophilic moiety. The pseudomycin compounds A, A', B, B', C, C' are represented by the formula I above where R is as defined below.

| Pseudomycin A | R = 3,4-dihydroxytetradecanoyl |
| Pseudomycin A' | R = 3,4-dihydroxypentadecanoate, |
| Pseudomycin B | R = 3-hydroxytetradecanoyl |
| Pseudomycin B' | R = 3-hydroxydodecanoate |
| Pseudomycin C | R = 3,4-dihydroxyhexadecanoyl |
| Pseudomycin C' | R = 3-hydroxyhexadecanoyl |

As used herein, pseudomycin refers to one or more members of a family of antifungal agents that has been isolated from the bacterium *Pseudomonas syringae*. A pseudomycin is a lipodepsipeptide, a cyclic peptide including one or more unusual amino acids and having one or more appended hydrophobic or fatty acid side chains. Specifically, the pseudomycins are lipodepsinonapeptides, with a cyclic peptide portion closed by a lactone bond and including the unusual amino acids 4-chlorothreonine, 3-hydroxyaspartic acid, dehydro-2-aminobutyric acid, and 2,4-diaminobutyric acid. It is believed that these unusual amino acids are involved in biological characteristics of the pseudomycins, such as stability in serum and their killing action. Pseudomycins include pseudomycin A, pseudomycin A', pseudomycin B, pseudomycin B', pseudomycin C, and pseudomycin C'. Each of these pseudomycins has the same cyclic peptide nucleus, but they differ in the hydrophobic side chain attached to this nucleus.

Pseudomycins A, A', B, B', C and C' have each been isolated and purified and their structures have been characterized by methods including amino acid sequencing, NMR, and mass spectrometry. Pseudomycins A, B, C, and C' are discussed in U.S. Pat. No. 5,576,298, issued Nov. 19, 1996 to G. Strobel et al.; Harrison et al., "Pseudomycins, a family of novel peptides from *Pseudomonas syringae* possessing broad-spectrum antifungal activity," *J. Gen. Microbiology* 137, 2857-2865 (1991); and Ballio et al., "Novel bioactive lipodepsipeptides from *Pseudomonas syringae*: the pseudomycins," *FEBS Lett*. 355, 96-100 (1994). Pseudomycins A' and B' are described in U.S. Pat. Application Ser. No. PCT/US00/08727, by Palaniappan Kulanthaivel, et al. entitled "Pseudomycin Natural Products" submitted even date herewith and exemplified in the Examples, and incorporated herein by reference in its entirety. Antifungal activity due to several pseudomycins was traced to *P. syringae* bearing a transposon known as Tn 903, which encodes factors including kanamycin resistance. The sequence of and methods for manipulating transposon Tn 903 are known. Oka et al., "Nucleotide sequence of the kanamycin resistance transposon Tn 903," *J. Mol. Biol*. 147, 217-226 (1981). Each of the references cited in this paragraph is specifically incorporated herein by reference.

The pseudomycins vary in structure and properties. Preferred pseudomycins A, B, C and C' exhibit activity against a wide variety of fungi and also exhibit generally acceptable toxicity. Compared to the other preferred pseudomycins, pseudomycin B has greater potency against certain fungi and a lower level of toxicity. Therefore, for the present methods, pseudomycin B is more preferred. Each pseudomycin has a cyclic nonapeptide ring having the sequence Ser-Dab-Asp-Lys-Dab-aThr-Dhb-HOAsp-ClThr (Serine; 2,4-Diaminobutyric acid; Aspartic acid; Lysine; 2,4-Diaminobutyric acid; alloThreonine; Dehydro-2-aminobutyric acid; 3-hydroxyAspartic acid; 4-chloroTheonine), more specifically, L-Ser-D-Dab-L-Asp-L-Lys-L-Dab-L-aThr-Z-Dhb-L-Asp(3-OH)-L-Thr(4-Cl), with the carboxyl group of the ClThr and the hydroxyl group of the serine closing the ring with a lactone bond. The pseudomycins differ in the nature of the lipophilic moiety that is attached to the amine group of the N-terminal serine. The amine group of the serine forms an amide bond with the carboxyl of a 3,4-dihydroxytetradecanoyl moiety in pseudomycin A, a 3-monohydroxytetradecanoyl moiety in pseudomycin B, a 3,4-dihydroxyhexadecanoyl moiety in pseudomycin C and a 3-monohydroxyhexadecanoyl moiety in pseudomycin C'. The carboxyl group of the serine forms an amide bond with the Dab of the ring.

The pseudomycins used in the present invention may be used as their acceptable salts. The term "acceptable salt", as used herein, refers to salts of the compounds described above that are substantially non-toxic to living organisms. Typical acceptable salts include those salts prepared by reaction of the compounds of the present invention with a mineral or organic acid or an inorganic base. Such salts are known as acid addition and base addition salts.

Acids commonly employed to form acid addition salts are mineral acids such as hydrochloric acid, hydrobromic acid, hydroiodic acid, sulfuric acid, and phosphoric acid, and organic acids such as p-toluenesulfonic, methanesulfonic acid, oxalic acid, p-bromophenylsulfonic acid, carbonic acid, succinic acid, citric acid, benzoic acid, and acetic acid. Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fiunarate, maleate, butyne-1, 4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycollate, tartrate, methanesulfonate, propanesulfonate, naphthalene-1-sulfonate, napthalene-2-sulfonate, and mandelate. Preferred pharmaceutically acceptable acid addition salts are those formed with mineral acids such as hydrochloric acid and hydrobromic acid, and those formed with organic acids such as maleic acid and methanesulfonic acid.

Base addition salts include those derived from inorganic bases, such as ammonium or alkali or alkaline earth metal hydroxides, carbonates, and bicarbonates. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, and calcium carbonate. The potassium and sodium salt forms are particularly preferred.

It should be recognized that the particular counterion forming a part of any salt of this invention is not of a critical nature, so long as the salt as a whole is pharmacologically acceptable and as long as the counterion does not contribute undesired qualities to the salt as a whole.

The present invention may be better understood with reference to the following examples. These examples are intended to be representative of specific embodiments of the invention, and are not intended as limiting the scope of the invention.

Biological Materials on Deposit

*P. syringae* MSU 16H is publicly available from the American Type Culture Collection, Parklawn Drive, Rockville, Md., USA as Accession No. ATCC 67028. *P. syringae* strains 25-B1, 7H9-1, and 67 H1 were deposited with the American Type Culture Collection on Mar. 23, 2000 and were assigned the following Accession Nos.:

| | |
|---|---|
| 25-B1 | Accession No. PTA-1622 |
| 7H9-1 | Accession No. PTA-1623 |
| 67H1 | Accession No. PTA-1621 |

The pseudomycins were isolated from liquid cultures of *Pseudomonas syringae*. *Pseudomonas syringae* is a plant-associated microbe producing a variety of phytotoxins and other complex peptides[1-3]. In the late 1980s, it was shown that *P. syringae* was producing antifungal agents. Basically, the concept that endosymbionts growing on the plant produce antifungal agents to protect the plant from fungal diseases. The pseudomycins were identified as the bioactive antifungal agents. A transposon-generated mutant of *P. syringae* wild type was shown to be hyper-producers of these natural products. These transposon mutants strains[4] developed at Montana State University were used successfully to inoculate elm trees to control Dutch Elm Disease[5-6]. In addition, these natural products have shown selective antifungal activity against diseases found on field crops, fruits and other plants (Tables 1-3). For example, the pseudomycins shows promising activity against *M. fijiensis* (*M. fijiensis* causing black sigatoka of bananas requires more fungicide and fungicide applications than any other plant disease in the world today. The pseudomycins were also shown to prevent premature spoilage of mangoes.

EXAMPLE 1

Reproducible large-scale production (kilograms) of these natural products has been successfully demonstrated. Purified samples of free base and alternative salt forms were prepared. Approximately, 34 fungal plant pathogens were used to evaluate the antifungal properties of pseudomycin A, B, B', C, C'. Inhibitory concentrations were measured at two-time points day 2 and 5.

TABLE 1

| Antifungal Activity tested with pathogens of interest: |
|---|
| a. *Alternaria helianthi* = leaf spot of sunflower |
| b. *Aphanomyces* sp. = root rot, seedling wilt of many plants including sugarbeets |
| c. *Bipolaris sorokiniana* = kernal blight of barley |
| d. *Botrytis alli* = gray mold neck rot of onion |
| e. *Cochliobolis carbonum* = leaf blight of corn |
| f. *Diplodia natalensis* = bunch rot of grapes |
| g. *Dreschslera portulacae* = leaf spot of portulacs✓ |
| h. *D. teres* = barley net blotch |
| i. *D. tritici-repentis* leaf spot of wheat |
| j. *Fusarium avenaceum* = root rot of several field crops |
| k. *F. culmorum* = *fusarium* blight or scab |
| l. *F. oxysporum* = *fusarium* vascular wilt |
| m. *F. solani* = root rot |
| n. *Geotrichum candidum* = tomato field rot✓ |
| o. *Monilinia fructicola* = brown rot of stone fruits |
| p. *Mycosphaeella fijiensis* = black sigatoka of banana✓ (FIG. 3) |
| q. *Penicillum roqueforti* = green mold of fruit in storage✓ |
| r. *Phyllosticta maydis* = yellow leaf spot of corn |
| s. *Phytophthoras* causing blight, rots decay |
| t. *Rhizoctonia solani* = *rhizoctonia* root rot |
| u. *Sclerotina sclerotiorum* = crown rot of many plant species |
| v. *Septoria tritici* = leaf blotch and glume blotch of wheat✓ (FIG. 5) |
| w. *Tapesia acuformis* = take all disease of wheat |
| x. *Ustilago maydis* = smut of corn✓ |
| y. *Verticillum dahlia* = *verticillum* wilt of many crops and tree species. |

= Very sensitive towards pseudomycins

Materials and Methods

Fungi to be tested were propagated on potato dextrose agar (PDA) plates at room temperature. Stock solutions of pseudomycins and depsipeptide were suspended in dimethylsulfoxide (DMSO) (Sigma) at 5 mg/ml and stored at −20C. Serial dilutions of compounds were done the day of the experiment. All serial dilutions were made in DMSO. Note: an initial experiment of pseudomycins B and B' in methanol was performed on some of the fungi, and several fungi showed inhibited growth in the presence of methanol. These are noted in the raw data section.

Assays were performed in 24-well cell culture clusters (Costar 3524), with 990 ul potato dextrose broth (PDB, Difco) and 10 ul of the compound to be tested in each well. Initial concentrations tested were 50-1.56 ug/ml (final concentration of pseudomycin). Actual concentrations of pseudomycins tested were 50, 25, 12.5, 6.25, 3.12 and 1.56 ug/ml. Each well was inoculated with the appropriate fungus. Unless noted, the fungal inoculum consisted of an ~4 $mm^2$ piece of PDA with fungal mycelium. The exceptions were as follows. *Ustilago maydis*: this fungus grows much like a yeast on PDA, and cells were scraped from the PDA stock plate, resuspended in PDB and 10 ul inoculum added to each well. *Monilinia* sp.: this fungal mycelium grows as a very loose sheet on top of PDA and would not adhere to agar blocks. Fungal mycelium was ground with a metal rod in 500 ul PDB and 10 ul inoculum was added to each well. *Mycosphaeella fijiensis, Septoria passerinii, Septoria tritici*: these fungi all grow very slowly and the results were difficult to score if a small piece of agar with fungal mycelium on it was used as an inoculum. For these fungi, the mycelium was ground with a metal rod in 500 ul PDB and 10 ul inoculum was added to each well.

Wells were scored for fungal growth at two days and five days. Some slow growing fungi were scored at later days for growth because assessment was not possible at two or five days. Growth was scored by comparison to a control consisting of fungus inoculated into 990 ul potato dextrose broth and 10 ul of DMSO (Dimethylsulfoxide). An additional control consisting of fungal inoculum in PDB only was performed to ensure that the DMSO was not inhibitory to fungal growth. DMSO did not affect any of the fungi tested, with the exception of *Drechslera portulacae*, where some inhibition was noted.

Any fungi that showed inhibition were retested. For assays that were repeated, new stock solutions were made from a second shipment of pseudomycins. Note that pseudomycin B' and depsipeptide stock solutions were remade from first shipment materials because these were not included in the second shipment. Several of these fungi showed no growth even at the lowest levels of pseudomycins added, and were retested a third time using lower levels of pseudomycins (2-0.0625 ug/ml final concentration of pseudomycin). Actual concentrations of pseudomycins tested were 2, 1, 0.5, 0.25, 0.125 and 0.0625 ug/ml. A-$PO_4$ and A-FB=pseudomycin A phosphate salt and free base respectively.

Table 2: Two day results—concentration indicated is lowest level of compound (ug /ml) that results is no growth. NI, no inhibition; p (partial), at least 50% inhibited; -, not determined. If number of assays was greater than one, number of assays performed on the fungus is noted in parentheses. For several slow-growing fungi, days elapsed before observation (if different than two) are noted.

| *Pseudomycin-* | A-$PO_4$ | A-FB | B | B' | C | C' |
|---|---|---|---|---|---|---|
| *Alternaria helianthi* (2x) | 25 | 25 | NI | 25 | p at 50 | p at 50 |
| *Aphanomyces* sp. (2x) | 50 | NI | p at 50 | 25 | 25 | 25 |
| *Bipolaris sorokiniana* | NI | NI | NI | NI | NI | NI |

-continued

| Pseudomycin- | A-PO₄ | A-FB | B | B' | C | C' |
|---|---|---|---|---|---|---|
| Botrytis alli (2x) | 50 | NI | NI | NI | NI | NI |
| Cochizobolus carbonum | NI | NI | NI | NI | NI | NI |
| Diplodia natalensis | NI | NI | NI | NI | NI | NI |
| Drechslera portulacae (3x) | 0.06 | 0.25 | 0.06 | 0.12 | 0.06 | 0.05 |
| Drechslera teres | NI | NI | NI | NI | NI | NI |
| Drechslera tritici-repentis (2x) | 50 | 25 | 50 | 50 | 50 | 50 |
| Fusarium avenaceum | NI | NI | NI | NI | NI | NI |
| Fusarium culmorum | NI | NI | NI | NI | NI | NI |
| Fusarium oxysporum cubense | NI | NI | NI | NI | NI | NI |
| Fusarium solani | NI | p at 50 | p at 50 | NI | p at 50 | NI |
| Geotrichim candidum (3x) | 12.5 | 3.12 | 1.56 | 25 | 3.12 | 1.56 |
| Monilinia sp. (2x) | 12.5 | 6.25 | 3.13 | 25 | 6.25 | 3.12 |
| Mycosphaeella fijiensis (Sigatoka) (7 day, 3x) | 1 | 0.5 | 0.5 | 0.5 | 1.56 | 1.56 |
| Mycosphaeella fijiensis (8088/88) (7 day, 3x) | 0.12 | 0.25 | 0.06 | 0.5 | 0.125 | 0.125 |
| Penicillium roqueforti (3x) | 0.5 | 1 | 0.5 | 1.56 | 1.56 | 1.56 |
| Pestalotiopsis microspora NE-32 | p at 50 | p at 50 | p at 50 | NI | NI | NI |
| Phoma chrysamthecola | — | — | — | — | — | — |
| Phyllosticta maydis | p at 50 | p at 50 | 50 | p at 50 | p at 50 | p at 50 |
| Phytophthora cactorum | NI | NI | NI | NI | NI | NI |
| Phytophthora cinnemani | NI | NI | NI | NI | NI | NI |
| Phytophthora parasitica | NI | NI | NI | NI | NI | NI |
| Phytophthora ultimum | NI | NI | NI | NI | NI | NI |
| Rhizoctonia solani (2x) | 6.25 | 6.25 | 6.25 | 6.25 | 25 | p at 50 |
| Sclerotinia sclerotiorum (2x) | NI | NI | p at 50 | NI | NI | 50 |
| Septoria passerinii (3x) | 0.125 | 0.06 | 0.06 | 0.5 | 0.06 | 0.06 |
| Septoria tritici (3x) | 0.25 | 0.25 | 0.06 | 0.5 | 0.125 | 0.125 |
| Stagonospora nodorum | NI | NI | NI | NI | NI | NI |
| Tapesia acuformis (2x) | 50 | NI | NI | NI | NI | NI |
| Tapesia yallundae (2x) | 25 | 12.5 | 25 | 6.25 | 25 | 6.25 |
| Uslilago maydis (3x) | 0.5 | 1 | 0.5 | 1.56 | 0.25 | 0.25 |
| Verticillium dahliae (2x) | p at 50 | 50 | 25 | NI | 25 | p at 50 |

Table 3: Five day results—concentration indicated is lowest level of compound (ug/ml) that results in no growth. NI, no inhibition; p (partial), at least 50% inhibited; -, not performed on the fungus is noted in parentheses. For several slow-growing fungi, days elapsed before observation (if different than five) are noted.

| Pseudomycin- | A-PO₄ | A-FB | B | B' | C | C' |
|---|---|---|---|---|---|---|
| Alternaria helianthi (2x) | 25 | 25 | 50 | 25 | NI | NI |
| Aphanomnyces sp. (2x) | p at 50 | NI | 50 | NI | 50 | p at 50 |
| Bipolaris sorokiniana | NI | NI | NI | NI | NI | NI |
| Botrytis alli (2x) | p at 50 | NI | NI | NI | NI | NI |
| Cochliobolus carbonum | NI | NI | NI | NI | NI | NI |
| Diplodia natalensis | NI | NI | NI | NI | NI | NI |
| Drechslera portulacae (3x, 9 day) | 0.06 | 0.25 | 0.06 | 0.25 | 0.06 | 0.5 |
| Drechslera teres | NI | NI | NI | NI | NI | NI |
| Drechslera tritici-repentis | p at 50 | NI | p at 50 | p at 50 | NI | NI |
| Fusarium avenaceum | NI | NI | NI | NI | NI | NI |
| Fusarium culmorum | NI | NI | NI | NI | NI | NI |
| Fusarium oxysporum cubense | NI | NI | NI | NI | NI | NI |
| Fusarium solani | NI | NI | NI | NI | NI | NI |
| Geotrichim candidum (3x) | 6.25 | 6.25 | 3.12 | 25 | 25 | 6.25 |
| Monilinia sp. (2x) | 12.5 | 12.5 | 6.25 | 25 | 12.5 | 6.25 |
| Mycosphaeella fijiensis (Sigatoka) (3x, 21 days) | 1 | 1 | 1 | 1 | 1.56 | 1.56 |
| Mycosphaeella fijiensis (8088/88) (3x, 21 days) | 0.25 | 0.25 | 0.12 | 1 | 0.25 | 0.25 |
| Penicillium roqueforti (3x) | 3.12 | 3.12 | 6.25 | 1.56 | 12.5 | p at 50 |
| Pestalotiopsis microspora NE-32 | NI | NI | p at 50 | NI | NI | NI |
| Phoma chrysamthecola | NI | p at 50 | p at 50 | p at 50 | NI | NI |
| Phyllosticta maydis | NI | NI | 50 | NI | NI | NI |
| Phytophthora parasitica | NI | NI | NI | NI | NI | NI |
| Phytophthora cinnemani | NI | NI | NI | NI | NI | NI |
| Phytophthora ultimum | NI | NI | NI | NI | NI | NI |
| Phytophthora cactorum | NI | NI | NI | NI | NI | NI |
| Rhizoctonia solani (2x) | 12.5 | 50 | 50 | 6.25 | p at 50 | p at 50 |
| Sclerotinia sclerotiorum (2x) | NI | NI | NI | NI | NI | p at 50 |
| Septoria tritici (3x) | 0.25 | 0.25 | 0.06 | 0.5 | 0.25 | 0.25 |
| Septoria passerinii (3x) | 0.12 | 0.06 | 0.06 | 0.5 | 0.06 | 0.06 |

| Pseudomycin- | A-PO$_4$ | A-FB | B | B' | C | C' |
|---|---|---|---|---|---|---|
| Stagonospora nodorum | NI | NI | NI | NI | NI | NI |
| Tapesia acuformis (2x) | 50 | NI | NI | NI | NI | NI |
| Tapesia yallundae (2x) | 50 | 25 | NI | 50 | NI | NI |
| Ustilago maydis (3x) | 1 | 1 | 0.5 | 3.12 | 0.25 | 0.25 |
| Verticillium dahliae (2x) | p at 50 | p at 50 | p at 50 | NI | p at 50 | p at 50 |

A review of the above experiments demonstrates that the fungi tested were best inhibited by one or several of the pseudomycins, rather than responding in the same manner to all of the compounds tested. Six fungi that showed no growth even at the lowest concentration of pseudomycins initially tested, 1.56 ug/ml. These fungi were retested with even lower concentrations of pseudomycins. E.g. *Drechslera portulacae* appeared to have no growth even at 0.0625 ug/ml pseudomycin A (PO4), B and C (9 days). Two different isolates of *Mycosphaeella fijiensis* responded differently to the lower doses of pseudomycins. The Sigatoka isolate appeared to be inhibited by each of the pseudomycins down to ~1 ug/ml. However, 8088/88 isolate was best inhibited by pseudomycin B, with no growth at 0.125 ug/ml at 21 days. *Septoria tritici* and *Septoria passerinii* were strongly inhibited by all the pseudomycins, with *S. tritici* showing no growth at 5 days at 0.0625 ug/ml pseudomycin B, and *S. passerinii* showing no growth at 5 days at 0.0625 ug/ml pseudomycin A (free base), B, C and C'. *Ustilago maydis* was best inhibited by either pseudomycin C or C', with no growth at 0.25 ug/ml at 5 days. Some of these fungi showed only minor growth inhibition at the highest levels of pseudomycins tested (e.g. *Alternaria helianthi, Aphanomyces* sp., *Botrytis alli, Sclerotinia sclerotiorum, Tapesia acuformis, Tapesia yallundae* and *Verticillium dahliae*). Several fungi showed good inhibition with one or several pseudomycins, but not all. These include *Rhizoctonia solani*, which was best inhibited by B' (no growth at 6.25 ug/ml at 5 days), *Monilinia* sp., best inhibited by B and C' (no growth at 6.25 ug/ml at 5 days), *Geotrichim candidum*, best inhibited by B (no growth at 3.12 ug/ml at 5 days) and *Penicillium roqueforti*, best inhibited by B' (no growth at 1.56 ug/ml at 5 days).

From this data, it can be concluded that the pseudomycins are a group of selective "natural" fungicides. Some fungi causing infections found in post harvest crops and other plant species are sensitive to the pseudomycins (e.g. *Penicillum* and *Geotrichum*). Pseudomycin shows impressive activity against *M. fijiensis* (bananas). Crude preps as well as purified materials have a potential role in plant disease control. Large scale production of the pseudomycins is feasible and relatively inexpensive to produce. Natural products are likely to be environmentally compatible and potentially safe

REFERENCES

1. A. Ballio, F. Bossa, D. DiGiorgio, P. Ferranti, M. Paci, P. Pucci, A. Scaloni, A. Segre, G. A. Strobel. *FEBS Letters*, 1994, 355, 96-100.
2. C. Potera. *Science*, 1994, 265, 605.
3. L. Harrision, D. B. Teplow, M. Rinaldi, G. A. Strobel. *J. General Microbiology* 1991, 137, 2857-2865.
4. B. Lam, G. Strobel, L. Harrison, S. Lam. *Proc. Natl. Acad. Sci.* 1987, 84, 6447-6451.
5. R. Scheffer, D. Elgersma, G. Strobel. *Neth. J. Pl. Path.* 1989, 95, 293-304.
6. R. Scheffer, D. Elgersma, L. A. DeWeger, G. Strobel. *Neth. J. Pl. Path.* 1989, 95, 281-292.

We claim:

1. A method for the protection or treatment of plants and crops against fungal related diseases caused by *Mycosphaerella* sp. which comprises applying to said plants or crops an effective amount of a *pseudomycin* composition, wherein the *pseudomycin* composition comprises a molecule having the chemical formula 1:

I wherein R is a lipophilic moiety.

2. The method according to claim 1, wherein the *pseudomycin* composition is isolated from *Pseudomonas syringae*.

3. The method according to claim 1 wherein said *pseudomycin* composition comprises an effective amount of molecules selected from the group consisting of *Pseudomycin* A, *Pseudomycin* A', *Pseudomycin* B, *Pseudomycin* B', *Pseudomycin* C, and *Pseudomycin* C'.

4. The method according to claim 1, wherein the *pseudomycin* composition is applied to said plants or crops as an aqueous suspension, solution or emulsion with a concentration ranging from about 1 to 100 micrograms per ml.

5. The method according to claim 1, wherein said *pseudomycin* composition is applied to plants and crops susceptible to *Mycosphaerella fijiensis* sp.

6. The method according to claim 1, wherein said plants and crops are selected from the group consisting of bananas, plantains, sunflower, sugar beets, barley, onion, grapes, portulacs, wheat, tomato and corn.

7. The method according to claim 4, wherein said applying comprises spraying the aqueous suspension, solution or emulsion directly onto said plants and crops.

8. The method of claim 1, wherein R is a 3,4-dihydroxytetradecanoyl moiety.

9. The method of claim 1, wherein R is a 3-monohydroxytetradecanoyl moiety.

10. The method of claim 1, wherein R is a 3,4-dihydroxyhexadecanoyl moiety.

11. The method of claim 1, wherein R is a 3-monohydroxyhexadecanoyl moiety.

* * * * *